(12) United States Patent
Baldi et al.

(10) Patent No.: US 11,684,690 B2
(45) Date of Patent: Jun. 27, 2023

(54) DEVICE FOR REDUCING POLLUTANTS IN A GASEOUS MIXTURE

(71) Applicant: CONSORZIO COLTECH, MONTELUPO FIORENTINO (IT)

(72) Inventors: Giovanni Baldi, Montespertoli (IT); Laura Niccolai, Montelupo Fiorentino (IT); Olivia Bitossi, Montespertoli (IT); Marco Bitossi, Montelupo Fiorentino (IT); Simone Bonari, Fucecchio (IT)

(73) Assignee: CONSORZIO COLTECH, Montelupo Fiorentino (IT)

( * ) Notice: Subject to any disclaimer, the term of this patent is extended or adjusted under 35 U.S.C. 154(b) by 610 days.

(21) Appl. No.: 16/651,443

(22) PCT Filed: Sep. 4, 2018

(86) PCT No.: PCT/IB2018/056721
§ 371 (c)(1),
(2) Date: Mar. 27, 2020

(87) PCT Pub. No.: WO2019/049019
PCT Pub. Date: Mar. 14, 2019

(65) Prior Publication Data
US 2020/0282097 A1 Sep. 10, 2020

(30) Foreign Application Priority Data

Sep. 6, 2017 (IT) .......................... 102017000099625
Sep. 6, 2017 (IT) .......................... 102017000099719

(51) Int. Cl.
*A61L 9/18* (2006.01)
*B01D 53/86* (2006.01)
(Continued)

(52) U.S. Cl.
CPC ............. *A61L 9/18* (2013.01); *B01D 53/8628* (2013.01); *B01D 53/8668* (2013.01); *B01J 21/04* (2013.01);
(Continued)

(58) Field of Classification Search
CPC ............... A61L 9/00; A61L 9/20; A61L 9/205
(Continued)

(56) References Cited

U.S. PATENT DOCUMENTS

| 4,766,321 A | * | 8/1988 | Lew | .......................... A61L 9/20 |
| | | | | 250/431 |
| 7,147,692 B2 | * | 12/2006 | Fornai | .................... B01D 50/60 |
| | | | | 96/290 |

(Continued)

FOREIGN PATENT DOCUMENTS

| EP | 2654927 A1 | 10/2013 |
| EP | 2666535 A1 | 11/2013 |

OTHER PUBLICATIONS

Clemens Burda, et al., "Enhanced Nitrogen Doping in TiO2 Nanoparticles", NANO Letters, American Chemical Society, vol. 3, No. 8, Jan. 1, 2003, pp. 1049-1051, XZP007908496.

*Primary Examiner* — Monzer R Chorbaji
(74) *Attorney, Agent, or Firm* — Pearne & Gordon LLP; Bryan M. Gallo

(57) ABSTRACT

Described is a device (1) for reducing pollutants in a gaseous mixture comprising: •a containment body (2) having an inlet portion (3) for the gaseous mixture and an outlet portion (4) for the gaseous mixture, the containment body (2) imposing on the gaseous mixture a fixed direction of flow (D), •at least one filtering unit (10) comprising a photocatalytic filter (7) interposed, along the fixed direction of flow (D), between a first light source (6a) and a second light source (6b), both having a wavelength in the visible spectrum (400-700 nm), the photocatalytic filter (7) comprising a photocatalytic
(Continued)

nanoparticle coating and the nanoparticle coating comprising titanium dioxide doped with a nitrogen doping agent. •a unit (5) for straightening the flow before the filtering unit (10).

10 Claims, 3 Drawing Sheets

(51) Int. Cl.
*F24F 8/167* (2021.01)
*A61L 101/02* (2006.01)
*A61L 101/12* (2006.01)
*A61L 101/18* (2006.01)
*A61L 101/24* (2006.01)
*A61L 101/28* (2006.01)
*B01J 21/06* (2006.01)
*B01J 21/04* (2006.01)
*B01J 21/08* (2006.01)
*B01J 35/00* (2006.01)
*B01J 37/02* (2006.01)

(52) U.S. Cl.
CPC ............ *B01J 21/063* (2013.01); *B01J 21/08* (2013.01); *B01J 35/004* (2013.01); *B01J 35/0013* (2013.01); *B01J 37/0215* (2013.01); *F24F 8/167* (2021.01); *A61L 2101/02* (2020.08); *A61L 2101/12* (2020.08); *A61L 2101/18* (2020.08); *A61L 2101/24* (2020.08); *A61L 2101/28* (2020.08); *A61L 2209/12* (2013.01); *A61L 2209/14* (2013.01); *A61L 2209/211* (2013.01); *A61L 2209/212* (2013.01); *A61L 2209/22* (2013.01); *B01D 2255/20707* (2013.01); *B01D 2255/802* (2013.01); *B01D 2257/404* (2013.01); *B01D 2257/708* (2013.01)

(58) Field of Classification Search
USPC ........................................ 422/24; 250/453.11
See application file for complete search history.

(56) References Cited

U.S. PATENT DOCUMENTS

| | | |
|---|---|---|
| 9,409,124 B2 | 8/2016 | Cohen et al. |
| 2003/0113246 A1* | 6/2003 | Saitou ............... A61L 9/014 422/123 |
| 2007/0041882 A1 | 2/2007 | Roseberry et al. |
| 2010/0086436 A1 | 4/2010 | Roseberry et al. |
| 2013/0312858 A1 | 11/2013 | Cohen et al. |
| 2015/0114822 A1 | 4/2015 | Greco |

* cited by examiner

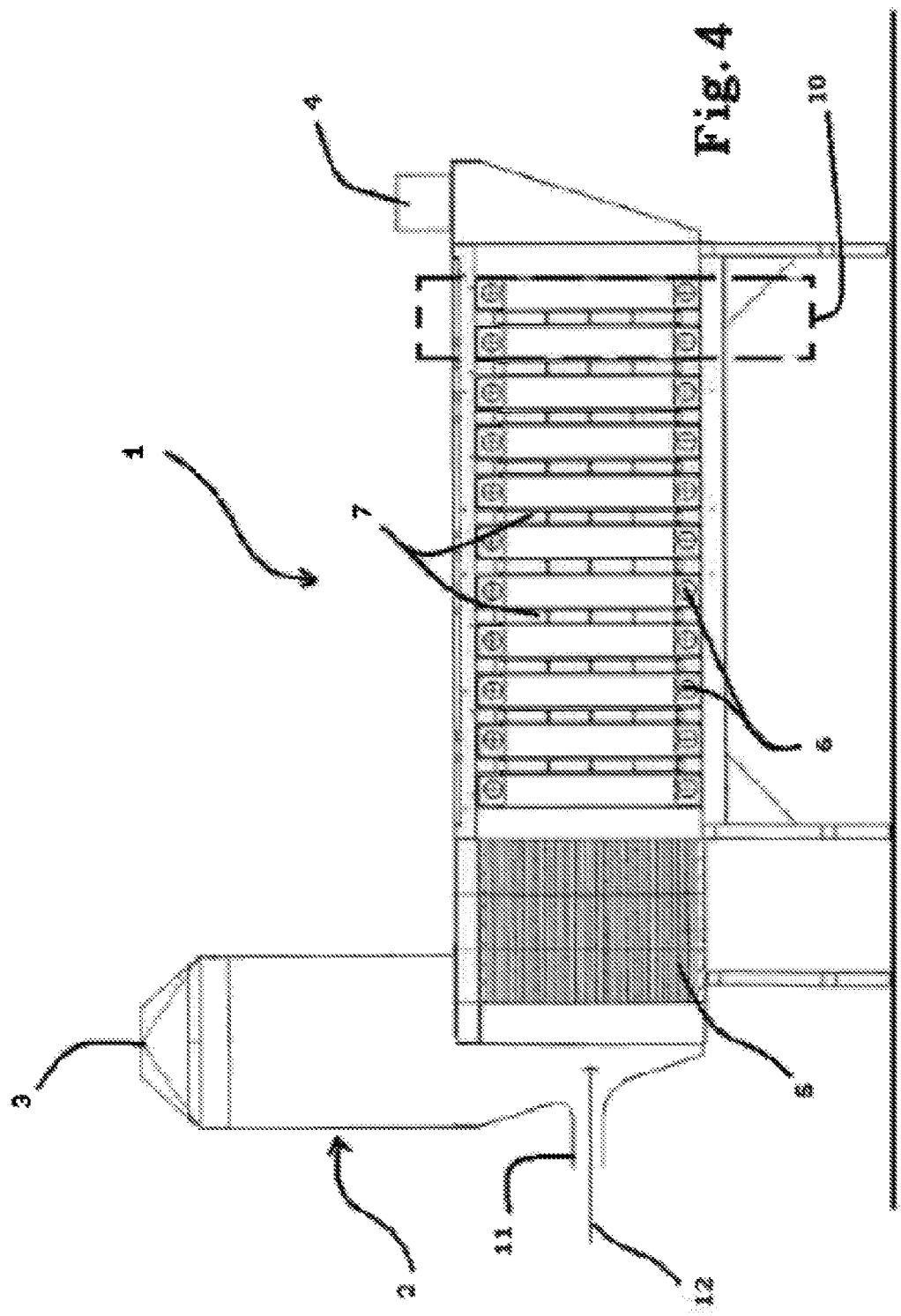

DEVICE FOR REDUCING POLLUTANTS IN A GASEOUS MIXTURE

TECHNICAL FIELD

This invention relates to a device for reducing pollutants in a gaseous mixture.

The development and diffusion of human activities has led, over the years, to an increasingly significant increase in the pollutant substances present in the air which is breathed.

More specifically, an increasing attention is dedicated to the effects which the pollutant emissions produced, for example, by production plants and means of transport have on the environment and on the ecosystems.

However, many studies have shown that the level of pollutants which accumulates in a closed space can be equal, if not even greater, to that present in the outside environment.

The substances most commonly present are in general nitric oxides (NOx) and comprise volatile organic compounds (VOCs), which can also have originated from commonly used household objects, such as: cleaning products, deodorants, air conditioning systems and interior decor.

The need to guarantee the comfort of both indoor and outdoor environments, both domestic and for work, without harming the health of the occupants, has lead to the study of devices which are able to remove or at least render innocuous all those substances which could be harmful for human health.

The need to guarantee a good air quality is felt even more in work environments, in which activities may be carried out which generate harmful substances for the operators and inside of which the operators must remain for many several hours a day.

BACKGROUND ART

There are currently devices for reducing pollutants which can be installed inside closed environments for reducing the pollutants below the risk threshold.

They are generally filtering devices which are inserted inside normal air ducts of the work environment.

The prior art devices usually have, as a filtering unit, photocatalytic filters, generally based on the use of a photocatalyst very often based on titanium dioxide, which are able, in the presence of oxygen and water, to efficiently degrade and oxidise the above-mentioned pollutant compounds present in the air.

This feature has made titanium dioxide a particularly used compound in the sector for manufacturing air filters, as it is able to significantly improve the quality of the air breathed in domestic and work environments.

More specifically, the anatase form of the titanium dioxide remains the most promising photocatalytically active semiconductor in this sector and many efforts have been made in the attempt to optimise the production and application processes of this particular crystalline form.

More in detail, the titanium dioxide has photocatalytic properties which can be activated when irradiated with a light having a wavelength in the ultraviolet zone, for example with a wavelength of between 300 and 390 nm, so that it is only able to activate 5% of the visible luminous radiation.

It follows that this type of devices has a very low efficiency, unless it is used in combination with ultraviolet lamps specifically designed and manufactured to perform the function of activating the titanium dioxide.

This also results in the fact that in order to obtain good performance levels for reducing the pollutants by means of the prior art filters it is necessary that they comprise a series of ultraviolet light sources, which are characterised by having significant energy consumptions and also low durability over time.

It is clear that on a filter device which must, by its very nature, operate continuously for the entire working day, this energy consumption is significant and problematic for the running costs of the system in which the device is installed.

Another major drawback of the ultraviolet light sources is the purchase cost and the relative low number of hours of service life, in particular if compared with the light sources in the visible spectrum of the LED type which are characterised by a very low energy consumption, a low purchase cost and at the same time a life cycle which is much greater than that of the other traditional light sources.

SUMMARY OF THE INVENTION

In this context, the technical purpose which forms the basis of this invention is to provide a device for reducing pollutants in a gaseous mixture which overcomes at least some of the above-mentioned drawbacks of the prior art.

The aim of this invention is to provide a device for reducing pollutants in a gaseous mixture characterised by a high efficiency in terms of elimination and reduction of pollutants in a gaseous mixture and which is at the same time inexpensive and reliable in daily use.

Moreover, a device for reducing pollutants in a gaseous mixture with these features can be designed not only for the treatment of pollutants in rooms but also for the treatment of gaseous emissions of an industrial type which require treatment before being introduced into the atmosphere.

The technical purpose indicated and the aims specified are substantially achieved by device for reducing pollutants in a gaseous mixture comprising the technical features described in one or more of the appended claims.

DESCRIPTION OF THE DRAWINGS

Further features and advantages of the invention are more apparent in the non-limiting description which follows of a preferred embodiment of a device for reducing pollutants in a gaseous mixture as illustrated in the accompanying drawings, in which:

FIG. 4 shows a second embodiment of a device according to the invention.

DETAILED DESCRIPTION

Figure 1:
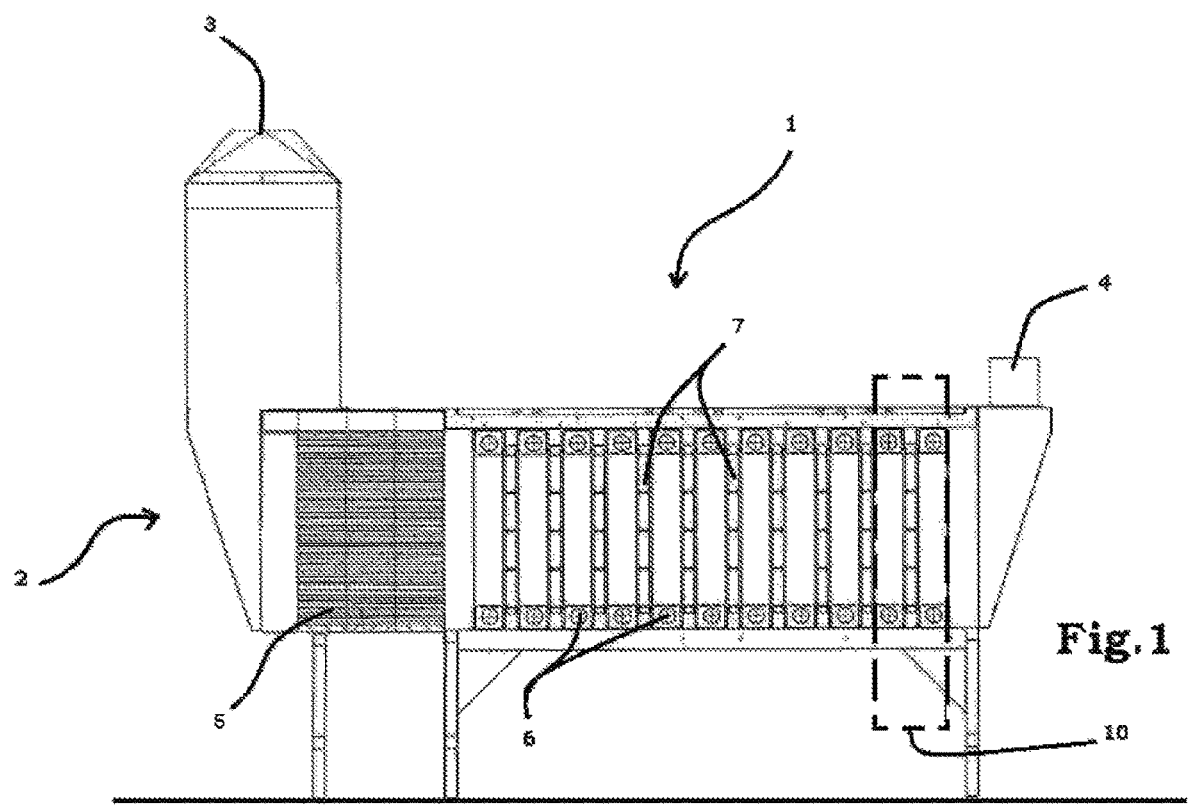
FIG. 1 shows a schematic cross-section and non-limiting example of a device for reducing pollutants in a gaseous mixture according to the invention.

The numeral 1 in FIG. 1 denotes in general a device 1 for reducing pollutants in a gaseous mixture, for example air, which comprises a containment body 2 having an inlet portion 3 and an outlet portion 4 of the gaseous mixture.

The containment body 2 may advantageously be connected in series with the aeration ducts of the building.

Figure 2:
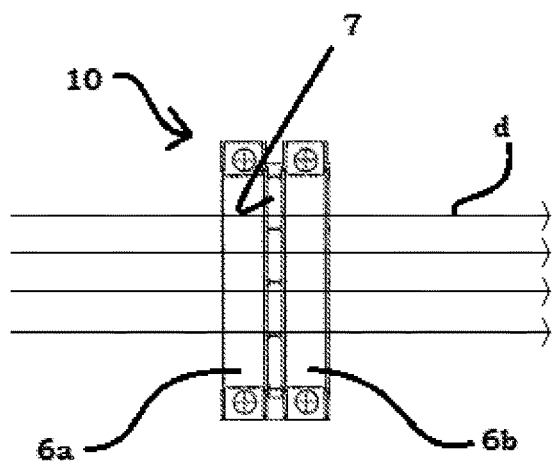
FIG. 2 shows a filtering unit used in a device according to the invention.

The containment body 2 creates a fixed physical path imposing a fixed direction of flow, indicated for simplicity only in FIG. 2 with the letter "d", on the gaseous mixture.

Advantageously, the containment body 2 comprises elements for resting on the ground.

Inside the containment body there is at least one filtering unit 10, shown schematically in FIGS. 1 and 2, which comprises a photocatalytic filter 7 interposed, along the fixed direction of flow "d" between a first light source 6a and a second light source 6b both with a wavelength in the visible spectrum.

The light sources 6, 6a, 6b may be of any known type, advantageously of the LED type.

The photocatalytic filter 7 comprises a photocatalytic nanoparticle coating which in turn comprises titanium dioxide doped with a nitrogen doping agent.

Preferably, the photocatalytic filter 7 is made of ceramic material and comprises at least one between: cordierite, mullite, alumina.

Moreover, preferably, the nitrogen doping agent is one between: amines, amides, organic ammonia salts, inorganic ammonia salts.

The filter 7 comprises an application surface and a photocatalytic nanoparticle coating configured for being deposited on the application surface.

The nanoparticle coating is made by depositing photocatalitically active nanoparticles, preferably using titanium dioxide nanoparticles in the anatase form.

Before being applied to the filter, the nanoparticle coating is doped by means of a nitrogen doping agent.

In other words, the application surface is coated with titanium dioxide in nanoparticle form doped with nitrogen.

As mentioned, the precursor used as nitrogen doping agent is preferably selected between: amine, amides, organic ammonium salts, inorganic ammonium salts.

The activation of the coating is carried out directly to the surface by heating at a temperature of around 500° C.

The presence of the nitrogen allows the band gap of the titanium dioxide to be modified, in particular reducing it, making the photocatalytic properties activatable by means of a large range of the spectrum of visible light and not only with the very limited ultraviolet component which occurs, for example, in the prior art devices.

Preferably, the application surface is made of ceramic material, which is particularly suitable as it provides an inert support which is very resistant and very porous, thus guaranteeing a long service life for the devices in which it is used.

As mentioned above, preferably the application surface is made using at least one between: cordierite, mullite, alumina.

In order to guarantee an optimum filtering result and maximise the efficiency of the filter 7, the application surface is made by means of a matrix of thin ceramic walls which define a plurality of parallel ducts, open at both ends, in such a way as to allow the passage of a gaseous mixture.

In other words, the application surface has a plurality of ducts, each of which is covered with the nanoparticle coating, thus defining a plurality of oxidisation sites in which, by activation of the photocatalytic properties of the nanoparticles of titanium dioxide doped with a nitrogen doping agent by an incident photon, the pollutants are absorbed and degraded, thereby obtaining a purification of the gaseous mixture, in particular air, passing through the ducts of the application surface.

For example, the nitrogen oxides undergo a degradation into nitrates, whilst other volatile organic substances are oxidised, forming carbonaceous residues and/or carbon dioxide.

The by-products resulting from the filtration of the air, which are not eliminated in the air flow, can be easily washed away from the application surface, thus restoring completely the operation.

The filtering unit 10 is advantageously of the tubular bundle type, that is to say, comprising a plurality of hollow tubular elements, inside of which the flow of gaseous mixture to be treated passes and positioned parallel to the above-mentioned fixed direction of flow "d".

Advantageously, the nanoparticle coating mentioned above extends at least to the inner surface of each tubular element constituting the tubular bundle.

Still more advantageously, a respective light source 6, 6a, 6b is positioned inside each tubular element.

In this embodiment the light sources 6, 6a, 6b are also positioned parallel to the fixed direction of flow "d".

Figure 3:
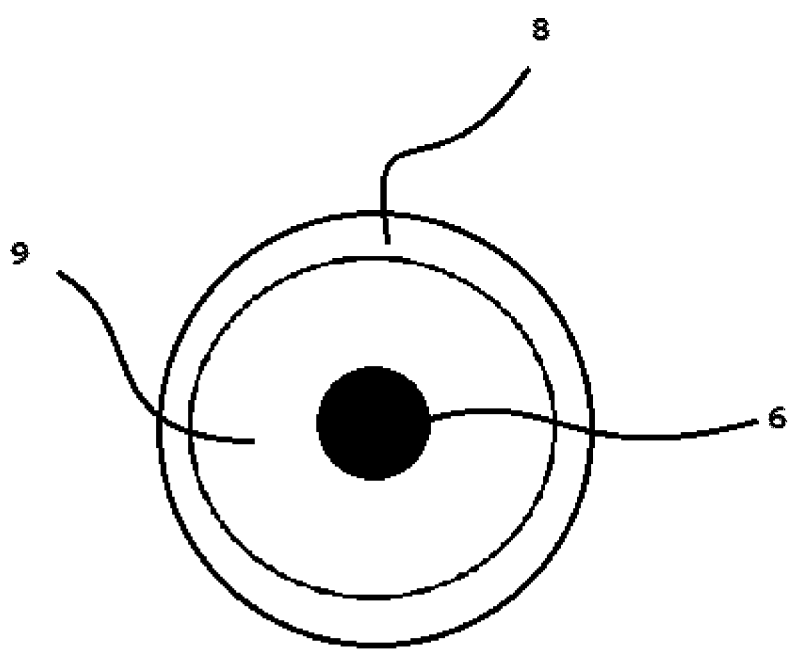
FIG. 3 shows a schematic view of an embodiment of a light source used in the device according to the invention.

With reference to FIG. 3, in the device 1 for reducing pollutants in a gaseous mixture according to this invention the light sources 6a, 6b may be positioned in such a way as to not be in direct contact with the flow of gaseous mixture as they are inserted inside a respective container 8.

The container 8 must be at least partly transparent to the visible light emitted by the light sources 6a, 6b.

Moreover, advantageously, between the container 8 and the light sources 6, 6a and 6b there is an air gap 9.

Inside the air gap 9 there is air at a pressure greater than the pressure of the flow of gaseous mixture.

In this way it is possible to obtain an additional safety in the case of fires or explosions.

The application of a device for reducing pollutants in a gaseous mixture with the features described above is not limited to the treatment of pollutants in rooms, where the concentrations never exceed the limits of explosiveness, but it may also be applied to the treatment of gaseous emissions of an industrial type which require treatment before being introduced into the atmosphere, and which, on the other hand, are very often mixtures which are defined as explosive. The configuration described with the air gap 9 allows the ATEX classification for the device.

In a preferred embodiment of the device 1 according to this invention, inside the containment body 2, in a position before the filtering unit 10 there is a device for straightening the flow 5 in such a way as to make the latter more homogeneous and, therefore, optimise the operation of the entire series of filtering units 10 present in the device 1.

More specifically, the device 5 for straightening the flow has the purpose of uniformly distributing the flow rate of the gaseous mass entering from the inlet portion 2 on the working section of the filtering unit 10 positioned after the straightening device 5.

Uniformly distributing the flow rate of the gaseous mass allows the contact between the mass and the filtering surface to be maximised, obtaining a greater overall efficiency during the reducing operation.

In order to optimise the operation, and therefore the reduction of the pollutants, by the filtering unit, the inner surfaces of the containment body 2 can be made reflective (or even mirror-like) with respect to visible light.

It is clear that this maximises the quantity of light emitted by the light sources 6, 6a, 6b.

Advantageously, moreover, the device 1 according to the invention comprises a recirculation circuit which connects, for example controlled by a control unit, the outlet portion 4 with the inlet portion 3 of the containment body 2.

The connection between the outlet portion 4 with the inlet portion of the containment body 2 may comprise a hollow duct controlled through the opening of a respective valve.

The valve is controlled in turn by one or more sensors positioned in the proximity of the outlet portion 4 configured to detect the actual percentage of pollutants in the gaseous mixture after the passage through the filtering unit 10.

In this way it is possible, for example if the sensors located in the outlet portion 4 detect a percentage of pollutants greater than a limit value, to transfer the flow of gaseous mixture again through the inlet portion 3 for a further passage through the filtering unit 10 rather than through the air duct in the building.

FIG. 4 shows a second solution according to which the device 1 comprises a containment body 2 having a first inlet portion 3 of the mixture which is not treated and an outlet portion 4 of the treated gaseous mixture. The containment body may advantageously be connected in series with the aeration ducts of the building.

The containment body 2 creates a fixed physical path imposing a fixed direction of flow, labelled "d'", on the gaseous mixture.

Inside the containment body 2 is at least one filtering unit 10, positioned in such a way as to be passed through by the gaseous mixture along the fixed direction of flow "d".

The containment body 2 also comprises a second inlet portion 11 of oxidising agents 12, positioned before the at least one filtering unit 10.

According to the embodiment shown in FIG. 4, the second inlet portion 11 designed for introducing oxidising agents inside the containment body 2 is located between the first inlet portion 3 of the gaseous mixture and the filtering unit 10.

According to a further alternative embodiment, the second inlet portion 11 of the oxidising agents 12 is located at, or coincides with the first inlet portion 3.

The oxidising agents 12 advantageously comprise one or more between: ozone, hydrogen peroxide or oxygen, hypochlorite and potassium permanganate.

During operation the oxidising agents 12 are introduced in a predetermined quantity inside the containment body 2 in such a way as to obtain a perfect mixing with the flow of gaseous mixture.

The mixing occurs before the flow passes through the filtering unit 10.

The oxidising agents 12 attack any odorous molecules included inside the gaseous mixture, causing a partial or total oxidisation, and a consequent reduction in the overall dimensions.

In short, the oxidising agents 12 perform a pre-treatment of the gaseous mixture before it passes through the filtering unit 10.

More specifically, when the oxidising agents comprise oxygen, ozone or hydrogen peroxide or hypochlorite or potassium permanganate a chain reaction of the oxidisation is obtained such that when the oxidising agents enter into contact with the activated titanium present on the photocatalytic filter 7 reinforced free radicals are generated, obtaining an increased reduction in the odorous emissions.

A gaseous mixture is therefore obtained at the outlet from the portion 4 from which both the odorous molecules and the pollutants have been removed.

The device according to this invention overcomes the limits of the prior art and achieves the preset aims.

The invention claimed is:

1. A device (1) for reducing pollutants in a gaseous mixture comprising:
   a containment body (2) having an inlet portion (3) for the gaseous mixture and an outlet portion (4) for the processed gaseous mixture, the containment body (2) imposing to the gaseous mixture a fixed direction of flow (D),
   at least one filtering unit (10) comprising a photocatalytic filter (7) interposed, along the fixed direction of flow (D), between a first light source (6a) and a second light source (6b), both having a wavelength in the visible spectrum, the photocatalytic filter (7) comprising a photocatalytic nanoparticle coating and the nanoparticle coating comprising titanium dioxide doped with a nitrogen doping agent, the device (1) also comprising a unit (5), positioned before the at least one filtering unit (10), for straightening the flow of the gaseous mixture, for uniformly distributing the flow rate of the gaseous mixture entering horizontally from said inlet portion (3) on the working section of said filtering unit (10), positioned after said unit (5);
   wherein the photocatalytic filter (7) is made of ceramic material and comprises at least cordierite and/or mullite; and
   wherein the nitrogen doping agent comprises at least ammine.

2. The device (1) for reducing pollutants in a gaseous mixture according to claim 1, wherein the light sources (6a, 6b) are not in direct contact with the flow of gaseous mixture upon insertion within a container (8), the container (8) being at least partly transparent to the visible light emitted by the light sources (6a, 6b).

3. The device (1) for reducing pollutants in a gaseous mixture according to claim 2, wherein there is an air gap (9) between the container (8) and the light sources (6, 6a, 6b).

4. The device (1) for reducing pollutants in a gaseous mixture according to claim 3, wherein inside the air gap (9) there is air at a pressure greater than the pressure of the flow of gaseous mixture.

5. The device (1) for reducing pollutants in a gaseous mixture according to claim 1, wherein the inner surfaces of the containment body (2) are at least partly reflective to the visible light.

6. The device (1) for reducing pollutants in a gaseous mixture according to claim 1, wherein the nanoparticle coating is obtained by in situ reaction at T>300° C.

7. The device (1) for reducing pollutants in a gaseous mixture according to claim 1, also comprising a recirculation circuit, the recirculation circuit connecting the outlet portion (4) with the inlet portion (3) of the containment body (2).

8. The device (1) for reducing pollutants in a gaseous mixture according to claim 1, wherein the containment body (2) comprises a second inlet portion (11) of oxidising agents (12), positioned before the at least one filtering unit (10).

9. The device (1) for reducing pollutants in a gaseous mixture according to claim 8, wherein the second inlet portion (11) is configured for mixing the oxidising agents (12) with the flow of the gaseous mixture.

10. The device (1) for reducing pollutants in a gaseous mixture according to claim 1, wherein the filtering unit (10) comprises at least one tubular filtering element positioned parallel to the fixed direction of flow (D).

* * * * *